Figure 1:
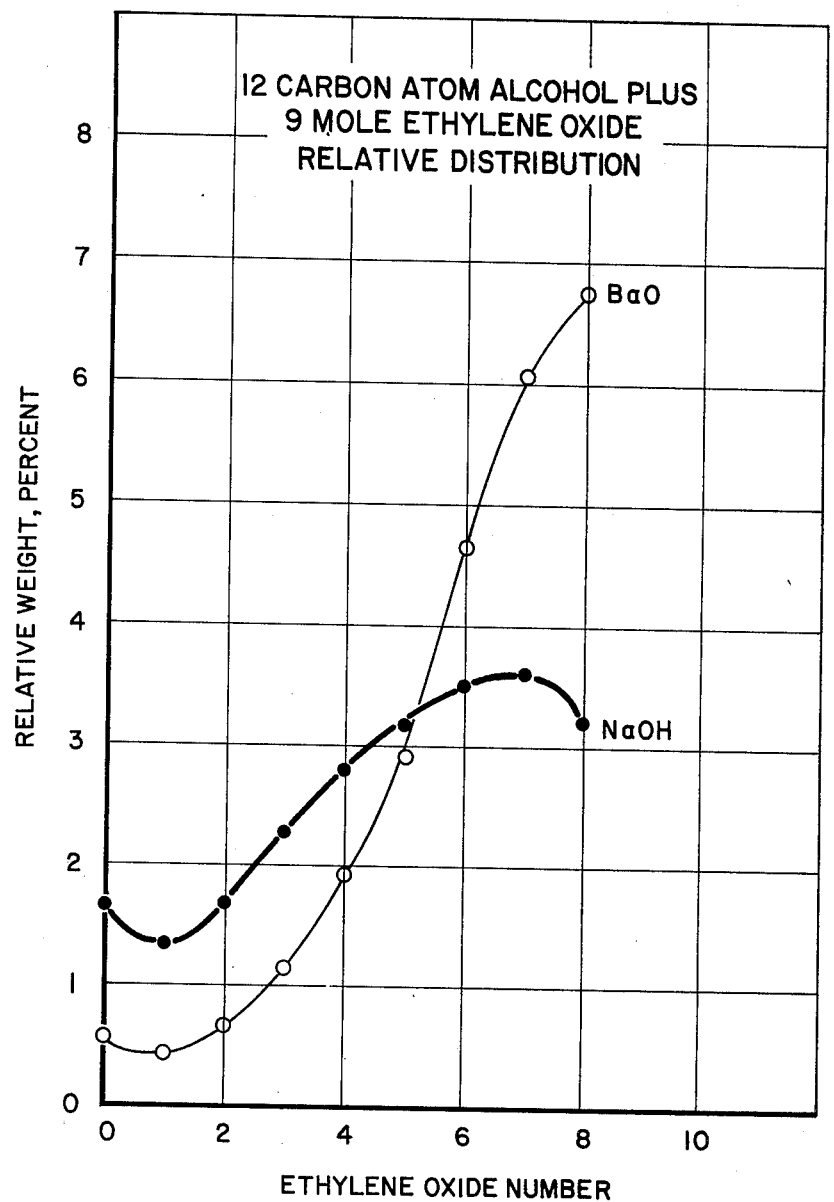

United States Patent [19]

Yang

[11] 4,239,917

[45] Dec. 16, 1980

[54] BARIUM OXIDE CATALYZED ETHOXYLATION

[75] Inventor: Kang Yang, Ponca City, Okla.

[73] Assignee: Conoco, Inc., Ponca City, Okla.

[21] Appl. No.: 54,322

[22] Filed: Jul. 2, 1979

Related U.S. Application Data

[63] Continuation-in-part of Ser. No. 916,421, Jun. 16, 1978, abandoned.

[51] Int. Cl.³ .............................................. C07C 41/03
[52] U.S. Cl. .................................... 568/618; 568/678
[58] Field of Search ................................ 568/618, 678

[56] References Cited

U.S. PATENT DOCUMENTS

| | | | |
|---|---|---|---|
| 3,328,306 | 6/1967 | Ellis | 252/99 |
| 3,475,499 | 10/1967 | Winnick | 568/618 |

*Primary Examiner*—Howard T. Mars
*Attorney, Agent, or Firm*—Cortlan R. Schupbach, Jr.

[57] ABSTRACT

Barium oxide is used as an ethoxylation catalyst for the reaction of ethylene oxide and alkanols of all classes. The reaction is carried out at temperatures of from about 200° to about 500° F. to yield the ethoxylated product. The product obtained has a very narrow, high adduct distribution with low levels of by-products and unreacted free alcohols. Calcium and magnesium oxides show no catalytic effect.

9 Claims, 12 Drawing Figures

BARIUM OXIDE CATALYZED ETHOXYLATION

This application is a continuation-in-part of application Ser. No. 916,421, filed June 16, 1978 now abandoned.

This invention relates to the production of ethoxylated alcohols by reacting said alcohols with ethylene oxide. More particularly, this invention relates to the production of ethoxylated alcohols by reacting said alcohols in the presence of a barium oxide catalyst.

The general reaction of alcohols and ethylene oxide to form ethoxylated alcohols or ethylene oxide adducts, has long been known and practiced on a commercial scale. For example, these ethylene oxide adducts have been used as detergents and cleaning agents, domestic and industrial laundry detergents, detergent builders, polishes, sanitizers, and dry cleaning materials. Other users include the pulp and paper industry, and the fiber industry. These materials are especially adapted to these uses since they have functional properties such as wetting power, foaming, emulsifying and dispersing abilities as well as solubilization and detergent abilities to facilitate their use.

Much literature is available in the general area of ethoxylation of alcohols. Many references are also available relating to the catalytic ability of various materials, and the mechanism and kinetics of these reactions. For example, French Pat. No. 1,365,945 teaches the use of compounds containing an active hydrogen atom reacted with ethylene oxide in the presence of alkali metal base. Acidic catalysts in general are also known. However, the ethoxylation of alcohols inevitably produces a distribution of various adducts. For example, in surfactant applications an adduct with too few ethylene oxide molecules is not effective because of poor solubility, while an adduct with too many ethylene oxide molecules is likewise undesirable because surface tension reduction per unit mass decreases drastically with increasing molecular weight. Thus it has long been essential to produce and use ethoxylates with as sharp a distribution in the desired mole adduce range (5 to 10) as possible. Acid catalyzed reactions such as that described above produce such ethoxylates, but these catalysts produce harmful side products such as dioxanes which must be separated and removed prior to use.

Russian Pat. No. 523,074 teaches that alkali metals and various carbonates can be used to catalyze this reaction. The side product formation in these base catalyzed reactions is very low, but in base catalyzed reactions the adduct distribution is undesirably broad, such that a large proportion of the product obtained is not useful.

Representative of, but not exhaustive of, the art in this area is U.S. Pat. No. 3,328,467 which describes the use of zeolites and modified zeolites as catalysts in ethoxylation reactions. French Pat. No. 1,557,407 uses triethyloxonium fluoroborate to catalyze such reactions. Indeed, the art abounds with references to alkali metal hydroxides, such as sodium and potassium hydroxide, tertiary amines and sodium metal. German Offenlegungsschrift No. 2,639,564 teaches polyalkylation of active hydrogen compounds in the presence of sodium trifluoroborate or perchlorates of metals such as magnesium, calcium, manganese or zinc. U.S. Pat. No. 3,969,417 uses tertiary oxonium salts as a catalyst. However, all these materials have the disadvantages described and set forth above.

It would therefore be of great benefit to provide a catalyst which provides the low by-product levels of base catalysts, yet has the narrow distribution of the preferred mole adducts obtained from acid catalysts. Such a catalyst, which would promote the narrowing of the product distribution curve, would contribute significantly to the intrinsic value of the ethoxylates produced.

It is therefore an object of the present invention to provide a catalyst which will yield a narrow, high mole adduct distribution from the reaction of alcohols of all classes with ethylene oxide while providing low levels of undesirable by-products and unreacted free alcohols. Other objects will become apparent to those skilled in this art as the description proceeds.

It has now been discovered according to the instant invention that ethoxylation of all classes of alkanols can be carried out in the presence of barium oxide, hydrated barium oxide, and other barium bases such as barium metal, providing a narrow distribution of high mole ethylene oxide adducts while yielding a very low level of free alcohols and undesirable by-products.

Thus, the instant invention describes a method for the ethoxylation of alcohols comprising contacting said alcohol with ethylene oxide in the presence of barium oxide catalyst. The instant invention is normally carried out at temperatures of from about 200° F. to about 500° F. Normally, the alcohols reacted under the process of the instant invention will contain from about 4 to about 18 carbon atoms but alcohols containing from about 10 to about 16 carbon atoms are those most used for commercial purposes.

While the instant invention is effective with all classes of alkanols, both primary, secondary, tertiary, linear and branched, linear and branched primary alkanols are the most commonly used alcohols and are the preferred alcohols of the instant invention. Representative examples of such alcohols are those derived by hydrogenation of natural fats and oils, such as CO and TA alcohols, trademark of and sold by Proctor and Gamble Co., such as CO-1214N alcohol, CO 1618 alcohol, and TA 1618 alcohol, and ADOL alcohols, trademark of and sold by Ashland Oil Co., such as ADOL 54 alcohol, ADOL 61 alcohol, ADOL 64 alcohol, ADOL 60 alcohol and ADOL 66 alcohol. Alcohols produced by Ziegler chemistry can also be ethoxylated. Examples of these alcohols are ALFOL alcohols, trademark of and sold by Continental Oil Co., such as ALFOL 1012 alcohol, ALFOL 1214 alcohol, ALFOL 1412 alcohol, ALFOL 1618 alcohol, ALFOL 1620 alcohol; and EPAL alcohols, trademark of and sold by Ethyl Chemical Co., such as EPAL 1012 alcohol, EPAL 1214 alcohol, EPAL 1418 alcohol. The invention is extremely useful for oxo alcohols (hydroformylation) produced from olefins. Examples of such alcohols are NEODOL alcohol, trademark of and sold by Shell Oil Co., such as NEODOL 23 alcohol, NEODOL 25 alcohol, NEODOL 1418 alcohol; TERGITOL-L, trademark of Union Carbide Corp., such as TERGITOL-L 125 alcohol; LIAL alcohols, trademark of and sold by Liquichimica Co. such as LIAL 125; and isodecyl and tridecyl alcohols, sold by Exxon Corp., such as isodecyl alcohol and tridecyl alcohol. Guebert alcohols can also be ethoxylated. Representative examples of these alcohols are STANDAMUL alcohols, trademark of and sold by Henkel Chemical Co., such as STANDAMUL GT-12 alcohol, STANDAMUL GT-16 alcohol, STANDAMUL GT-20 alcohol, STANDAMUL GT- 1620 alcohol. Secondary alcohols can also be used, such as TERGITOL 15 alcohol, trademark of and sold by Union Carbide Corp.

Generally, useable alcohols include 1-decanol; 1-undecanol; 1-dodecanol; 1-tricecanol; 1-tetradecanol; 1-pentadecanol; 1-hexadecanol; 1-heptadecanol; 1-octadecanol; 1-nonadecanol; 1-eicosanol; 1-dicosanol; 2-methyl-1-undecanol 2-propyl-1-nonanol; 2-butyl-1-octanol; 2-methyl-1-tridecanol; 2-ethyl-1-dodecanol; 2-propyl-1-undecanol; 2-butyl-1-decanol; 2-pentyl-1-nonanol; 2-hexyl-1-octanol; 2-methyl-1-pentadecanol; 2-ethyl-1-tetradecanol; 2-propyl-1-tridecanol; 2-butyl-1-dodecanol; 2-pentyl-1-undecanol; 2-hexyl-1-decanol; 2-heptyl-1-decanol; 2-hexyl-1-nonanol; 2-octyl-1-octanol; 2-methyl-1-heptadecanol; 2-ethyl-1-hexadecanol; 2-propyl-1-pentadecanol; 2-butyl-1-tetradecanol; 1-pentyl-1-tridecanol; 2-hexyl-1-dodecanol; 2-octyl-1-decanol; 2-nonyl-1-nonanol; 2-dodecanol; 3-dodecanol; 4-dodecanol; 5-dodecanol; 6-dodecanol; 2-tetradecanol; 3-tetradecanol; 4-tetradecanol; 5-tetradecanol; 6-tetradecanol; tetradecanol; 7-tetradecanol; 2-hexadecanol; 3-hexadecanol; 4-hexadecanol; 5-hexadecanol; 6-hexadecanol; 7-hexadecanol; 8-hexadecanol; 2-octadecanol; 3-octadecanol; 4-octadecanol; 5-octadecanol; 6-octadecanol; 7-octadecanol; 8-octadecanol; 9-octadecanol; 9-octadecanol-1; 2,4,6-trimethyl-1-heptanol; 2,4,6,8-tetramethyl-1-nonanol; 3,5,5-trimethyl-1-hexanol; 3,5,5,7,7-pentamethyl-1-octanol; 3-butyl-1-nonanol; 3-butyl-1-undecanol; 3-hexyl-1-undecanol; 3-hexyl-1-tridecanol; 3-octyl-1-tridecanol; 2-methyl-2-undecanol; 3-methyl-3-undecanol; 4-methyl-4-undecanol; 2-methyl-2-tridecanol; 3-methyl-3-tridecanol; 4-methyl-3-tridecanol; 4-methyl-4-tridecanol; 3-ethyl-3-decanol; 3-ethyl-3-dodecanol; 2,4,6,8-tetramethyl-2-nonanol; 2-methyl-3-undecanol; 2-methyl-4-undecanol; 4-methyl-2-undecanol; 5-methyl-2-undecanol; 4-ethyl-2-decanol; 4-ethyl-3-decanol.

While pressure or lack of pressure is not a detriment to the process of the instant invention, normally a pressure of up to about 100 pounds per square inch gauge (psig) can be used. Preferred pressures would be from about 10 to about 50 psig.

The instant invention is normally carried out at temperatures of from about 200° to about 500° F. However, for practical reasons, commercial operations will normally be carried out at temperatures in the range of from about 300° to about 400° F. and the most preferred temperature is around 350° F.

The reaction products of the described reaction can have any desired content of ethylene oxide but will normally range from about 30 to about 80% content of ethylene oxide (EO) based on weight. However, for most purposes the content of ethylene oxide will range from about 40% to about 70%. The amount of EO present in the reaction is not critical other than the minimum amount necessary to provide sufficient units to reach the mole adduct level desired for the alcohol present. Excess EO does not affect the reaction.

The barium oxide catalyst of the instant invention is a basic catalyst which provides a sharp distribution as to the mole adducts formed while reducing greatly the amount of unreacted free alcohols and undesirable by-products normally found in sharp distribution reactions. Barium oxide appears to be unique since tests carried out with metal oxides of calcium and magnesium failed to reveal any significant ethoxylation capacity.

For the purposes of the instant invention the barium oxide catalyst can be barium oxide alone, barium metal, barium hydroxide, and barium hydroxide hydrates. Any of these barium compounds are effective in the process of the instant invention. When used, these catalysts can be used in any desired quantity. The larger the quantity used, the more quickly the reaction goes to completion, although larger quantities do no appear to significantly alter the distribution obtained. However, for practical reasons, normally from about 0.1 to about 0.5 weight percent based upon the weight of the alcohol to be reacted will be present in the reactor. However, it must be very clear that these limits can be varied substantially since the catalyst is effective at all levels and that catalyst concentration is simply a reaction rate modifier and not a reaction distribution modifier.

Representative examples of such barium-containing catalysts are BaO, Ba(OH)$_2$, and BA(OH)$_2$.XH$_2$O wherein X represents the number of water molecules present. X is not a critical number.

Generally, treatment of alcohols with ethylene oxide yields a non-ionic detergent since hydrogen bonding to the numerous oxygen atoms makes the polyether end of the molecule water soluble. Alternatively, the ethoxylates can be converted into sulfates and used in the form of sodium salts.

The instant invention thus provides the production of highly efficient alcohol ethoxylates from primary, secondary, and tertiary branched chain and straight chain alkanols in a novel, highly unexpected manner. The ethoxylate products normally have from about 4 to about 20 carbon atoms. The reaction products are useful as a nonionic surface active agents with high wetting power which are composed of mixtures of monoalkyl ethers of polyethylene glycol.

Thus in the preferred form of the instant invention, ethylene oxide is reacted with a branched chain or straight chain higher alkanol in the presence of barium oxide, barium hydroxide, or other barium bases.

The invention is more concretely described with reference to the examples below, wherein all parts and percentages are by weight unless otherwise specified. The examples are provided to illustrate the instant invention and not to limit it.

EXAMPLE 1

The ethoxylations were carried out in a stirred autoclave. Experimental conditions are summarized in Table 1. Ethylene oxide (EO) was added as a liquid against a constant nitrogen back pressure through a control valve. As the EO reacted with the alcohols present, the pressure in the reactor was reduced, and additional EO was added through the control valve until desired pressure was again obtained. Thus a constant pressure, self-adjusting reaction tool place. FIG. 1 compares the distributions obtained from barium oxide and sodium hydroxide catalyzed reactions showing results as area percent by gas chromatograph (GC). An examination of the figure will show the extremely sharp distribution produced by barium oxide as compared to sodium hydroxide.

TABLE 1

| ETHOXYLATION OF C$_{12}$ ALCOHOL | | |
|---|---|---|
| Catalyst | NaOH | BaO |
| ALFOL/g | 200.0 (1.07 mole) | 200.0 (1.07 mole) |
| EO/g | 426.0 (9.67 mole) | 426.0 (9.67 mole) |
| Cat./g | 0.2 | 0.3 |

TABLE 1-continued

| ETHOXYLATION OF C$_{12}$ ALCOHOL | | |
|---|---|---|
| Catalyst | NaOH | BaO |
| EO Press./psig | 40 | 40 |
| Temp./°F. | 350 | 400 |
| Reaction Time/Hr | 6.5 | 2.0 |

EXAMPLE 2

Figure 2:
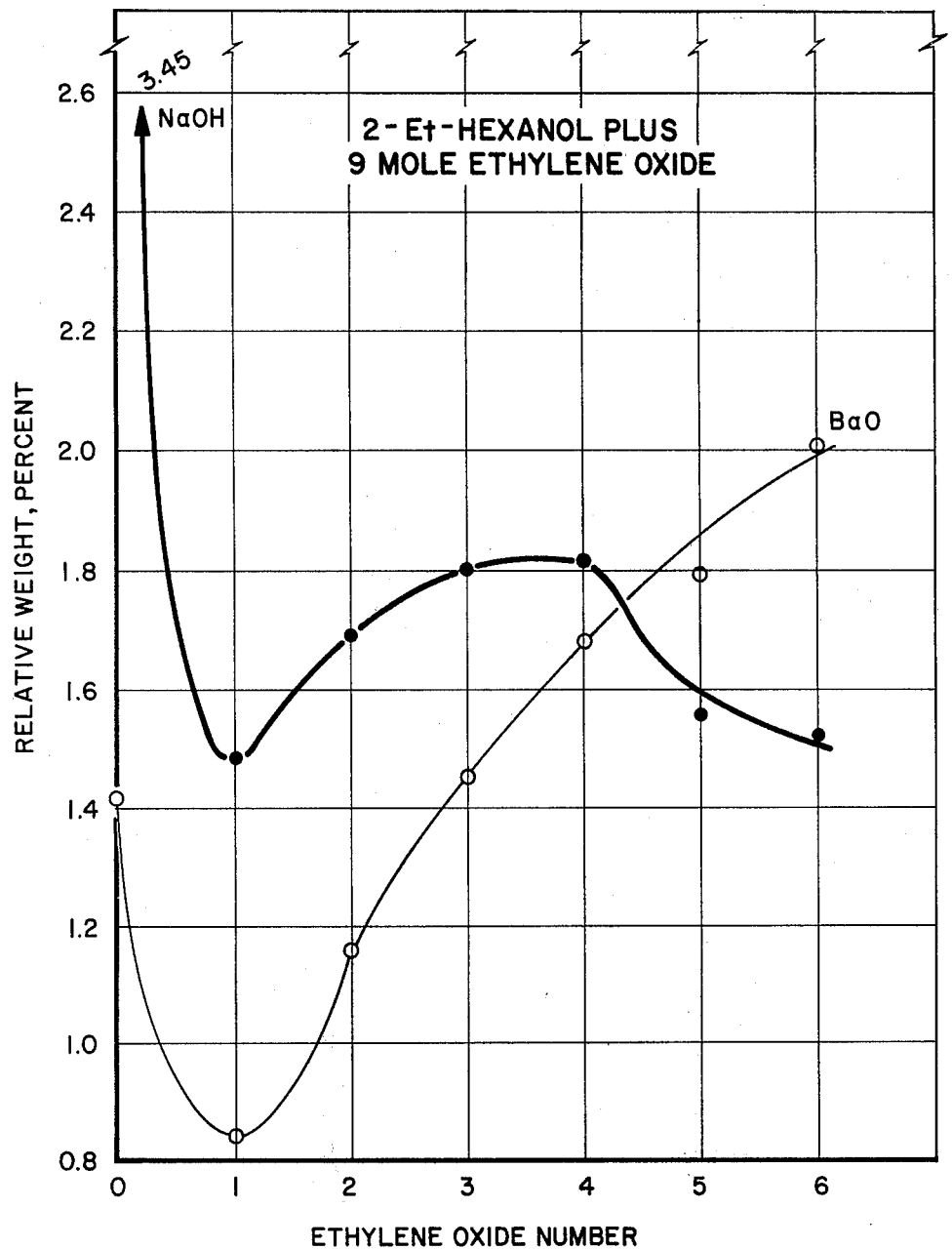

Table II summarizes experimental conditions used in the ethoxylation of 2-ethylhexanol-1. Again reference is made to the reaction conditions of the table and to FIG. 2 which shows the very narrow distribution obtained with barium hydroxide as compared to sodium hydroxide.

TABLE 2

| ETHOXYLATION OF Et-HEXANOL-1 | | |
|---|---|---|
| Catalyst | NaOH | BaO |
| Alcohol/g | 75.0 (0.576 mole) | 75.0 (0.576 mole) |
| EO/g | 228.0 (5.18 mole) | 228.0 (5.18 mole) |
| Cat./g | 0.08 | 0.15 |
| EO Press./psig | 50 | 50 |
| Temp./°C. | 173 (343° F.) | 201 (394° F.) |
| Reaction Time/Hr. | 4.5 | 2.0 |

In the figures, the EO number was determined using well-known gas chromatographic (GC) techniques.

EXAMPLE 3

The base catalyzed ethoxylation of C$_{10}$ alcohols produced as straight chain primary alcohols of even carbon numbers under a modified Ziegler-Natta polymerization of ethylene (sold as ALFOL 10 alcohols, trademark of and produced by Continental Oil Company) was carried out under the reaction conditions described in Table 3.

TABLE 3

| ETHOXYLATION OF ALFOL 10 | | | |
|---|---|---|---|
| Catalyst | NaOH | BaO | Ba(OH)$_2$ . 8H$_2$O |
| Alcohol/g | 300 | 300 | 300 |
| EO/g | 251 | 251 | 251 |
| Cat./g | 0.3 | 1.0 | 2.0 |
| EO pressure/psig | 20 | 20 | 20 |
| Temp/F | 400 | 400 | 400 |
| Reaction time/hr. | 2.8 | 2.3 | 3.7 |

Weight percents of the ethylene oxide units adducted onto the alcohol are shown in Table 4. The weight percent was determined using high pressure liquid chromatography (HPLC).

TABLE 4

| | RELATIVE WEIGHT PERCENT | | |
|---|---|---|---|
| EO Unit | NaOH | BaOH | Ba(OH)$_2$ . 8H$_2$O |
| 0 | 12.74 | 9.76 | 9.38 |
| 1 | 9.56 | 8.15 | 8.61 |
| 2 | 10.47 | 11.40 | 12.76 |
| 3 | 10.47 | 13.52 | 15.19 |
| 4 | 9.26 | 12.61 | 14.08 |
| 5 | 7.18 | 9.08 | 10.19 |
| 6 | 5.64 | 4.86 | 5.81 |
| 7 | 3.54 | 1.10 | 2.76 |
| 8 | 1.56 | — | 0.76 |

EXAMPLE 4

Calcium hydroxide (3.0 g) was dispersed in 300 g of a 10 carbon atom alcohol (ALFOL 10 trademark of and sold by Continental Oil Company) in a 1000 cc autoclave. After degassing at 200° F. by purge-and-pump, ethylene oxide was introduced at 350° F. through a control valve set at 20 psig back pressure. No reaction occurred in 1 hour. Temperature was raised to 400° F. No reaction was observable in 1 hour.

EXAMPLE 5

Magnesium oxide (20.0 g) and Mg-metal (2.0 g) was dispersed in 300 g alcohol and an attempt was made to initiate ethoxylation, all as described in Example 4. The reaction rate was neglegible at 350°, 400°, and 450° F.

EXAMPLE 6

Strontium hydroxide (0.3 g) was dispersed in 120 g of a 12 to 14 carbon atom alcohol (ALFOL 1214, trademark of and sold by Continental oil Company) in a stirred reactor. After degassing by purge-and-pump at 350° F., ethylene oxide was introduced at 350° F. through a control valve set at 40 psig back pressure. No reaction occurred in 1 hour.

EXAMPLE 7

Figure 11:
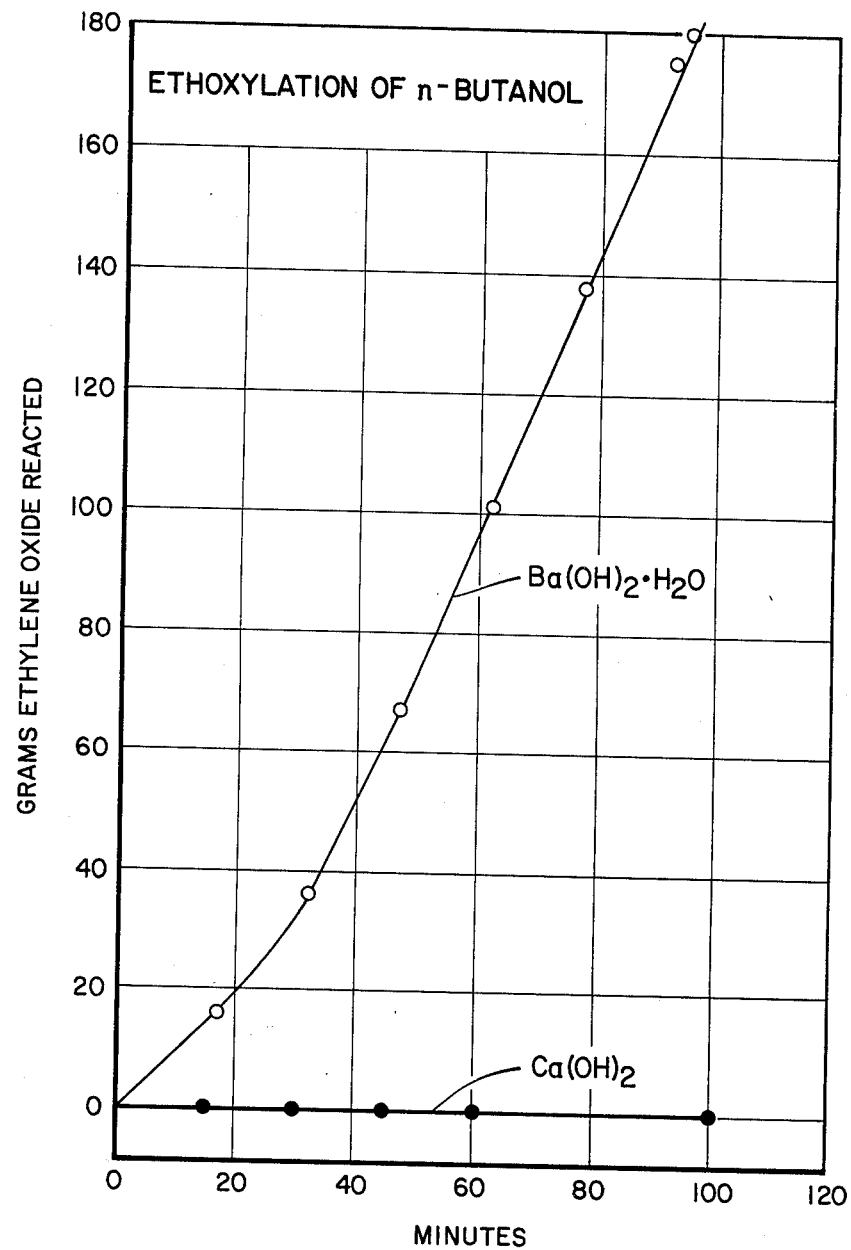

A carbon atom alcohol (butanol-1, 150.0 g) and Ba(OH)$_2$.H$_2$O(0.3 g) were introduced into a stirred reactor. After evacuation at room temperature, ethylene oxide was introduced at 150° C. and 60 psig total pressure. FIG. 11 shows the rate of ethoxylation. When (Ca(OH)$_2$(0.3 g) was used instead of Ba(OH)$_2$.H$_2$O, the ethoxylation rate was negligible.

EXAMPLE 8

Figure 12:
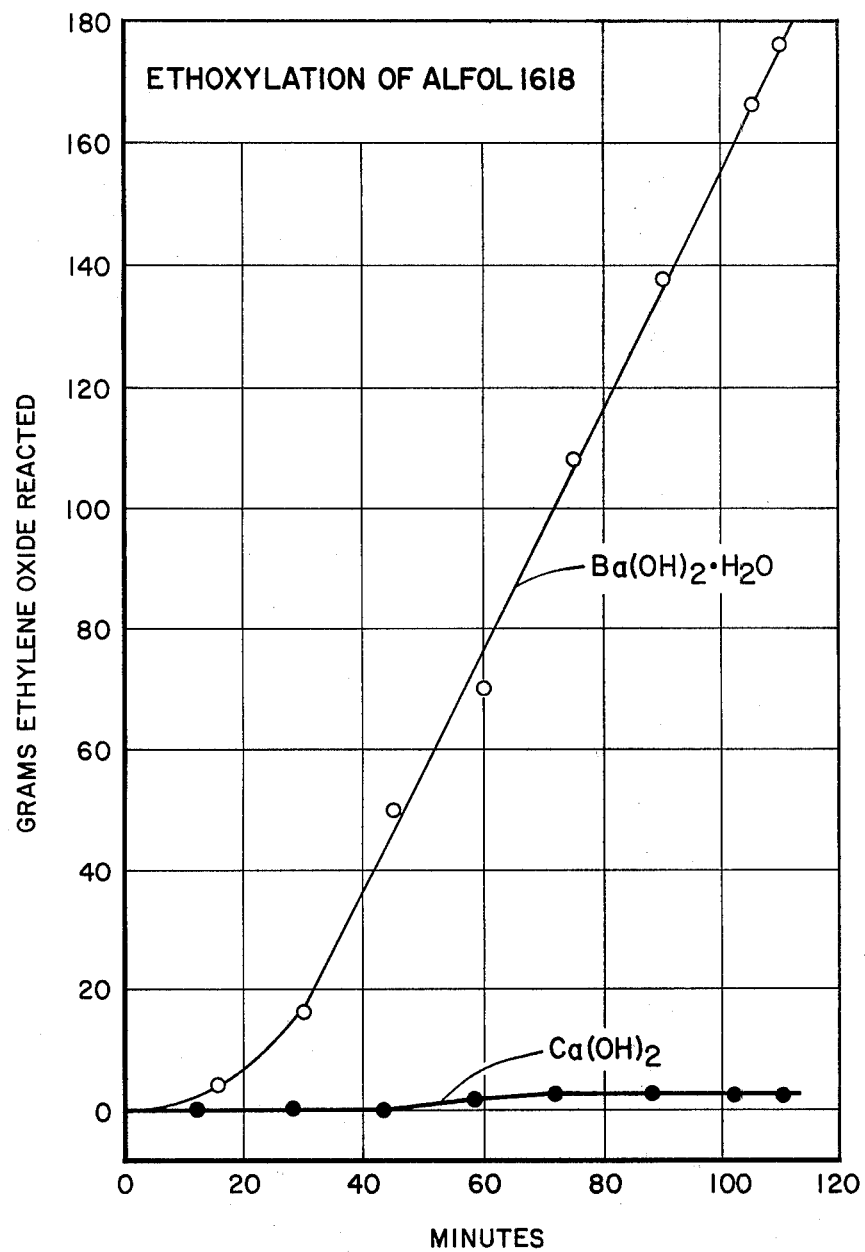

A 16 to 18 carbon atom alcohol (ALFOL 1618 trademark of and sold by Continental Oil Company, 120 g) and Ba(OH)$_2$.H$_2$O(0.3 g) were introduced into a stirred reactor. After purging at 150° C., ethylene oxide was introduced at 178° C. and 40 psig EO pressure. FIG. 12 shows the rate of ethoxylation. As shown in FIG. 12 the rate with Ca(OH)$_2$ was negligibly small as compared to the rate with Ba(OH)$_2$.H$_2$O.

It has also been surprisingly discovered that the catalyst and method of the instant invention is extremely well suited for ethoxylation of alcohols produced from olefins by hydroformylation/hydrogenation. Such alcohols have in the past presented difficulty when used as reactants for ethoxylation because of high concentration of unreacted alcohols.

However, the catalysts of the instant invention produce an extremely good ethoxylate using these products, as shown by comparative examples 9 through 16, where NaOH represents prior art catalysts.

EXAMPLE 9

Figure 3:
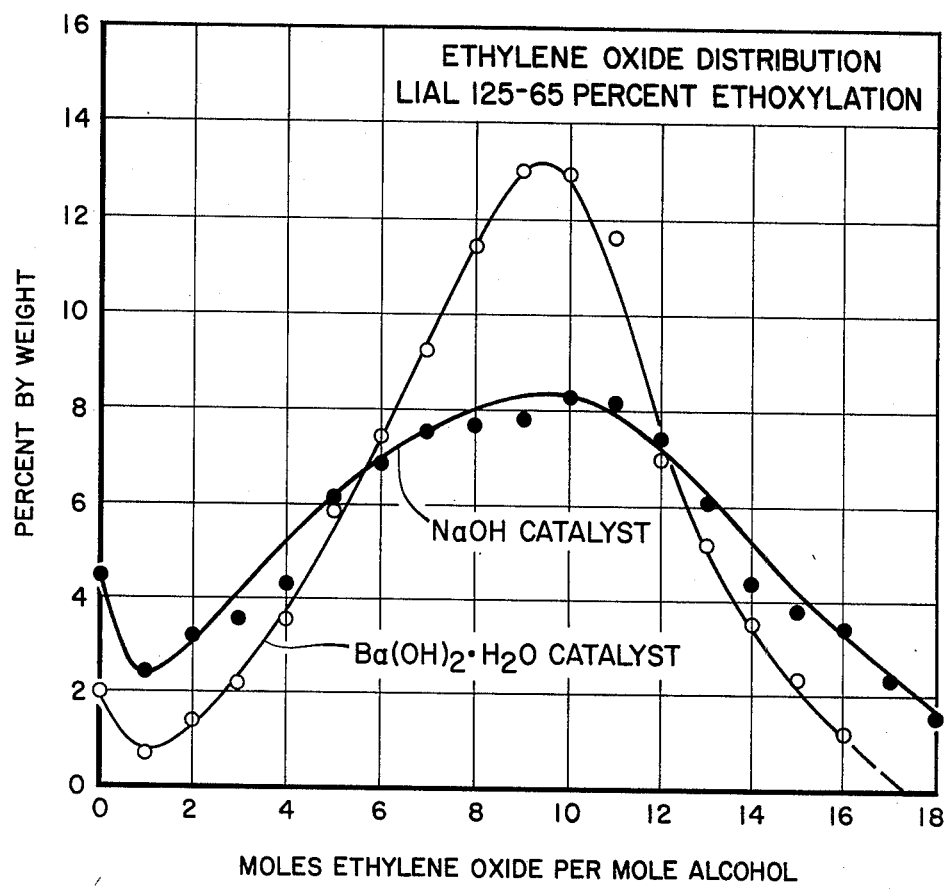
Figure 4:
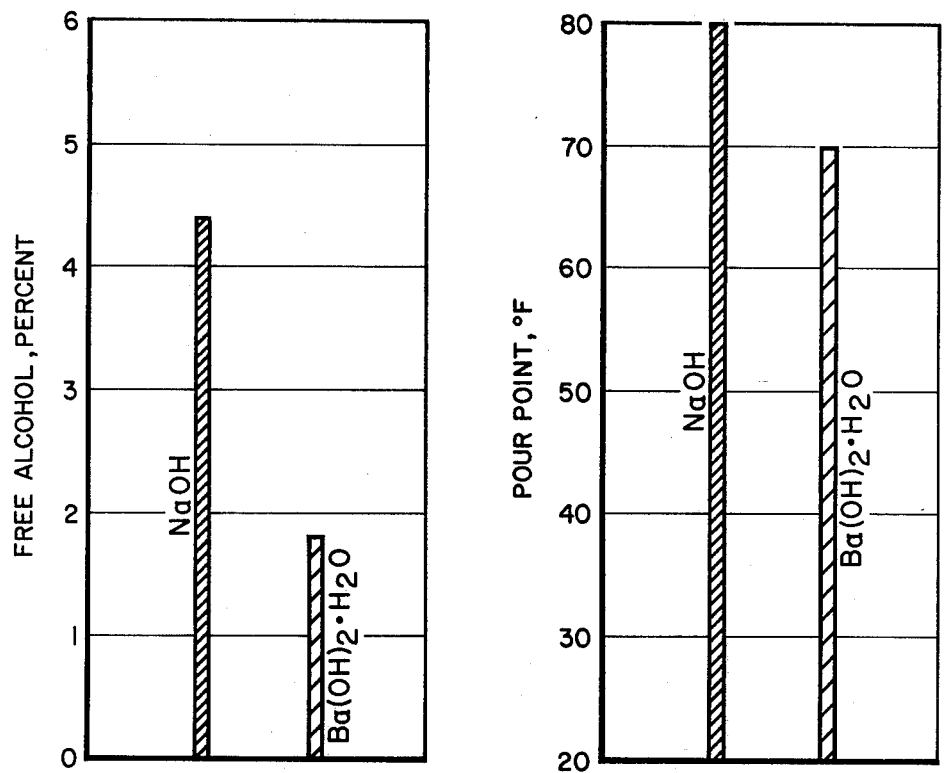

A stainless steel reactor (600 cc) was charged with LIAL 125 alchol (trademark of and sold by Liquichimica Co., Italy) (105 g) and Ba(OH)$_2$.H$_2$O (0.3 g) catalyst. After purging with N$_2$ at 250 cc/minutes for one hour at 150° C., the reactor was evacuated and the temperature was raised to 170° C. Ethylene oxide was then introduced to a total pressure of 40 psig, and EO uptake of 195 grams (65% ethoxylation) was allowed to proceed at this pressure. After ethoxylation, the catalyst was neutralized with acid and removed by centrifugation. EO distribution, free alcohol and pour point data are shown in FIGS. 3 and 4.

EXAMPLE 10

An experiment was performed as in Example 9 but with NaOH (0.15 g) catalyst. Acetic acid was used to neutralize the catalyst and centrifugation was omitted since the resulting salt was soluble. EO distribution, free alcohol and pour point data show the preferred results achieved from Example 9. See FIGS. 3 and 4).

EXAMPLE 11

Figure 5:
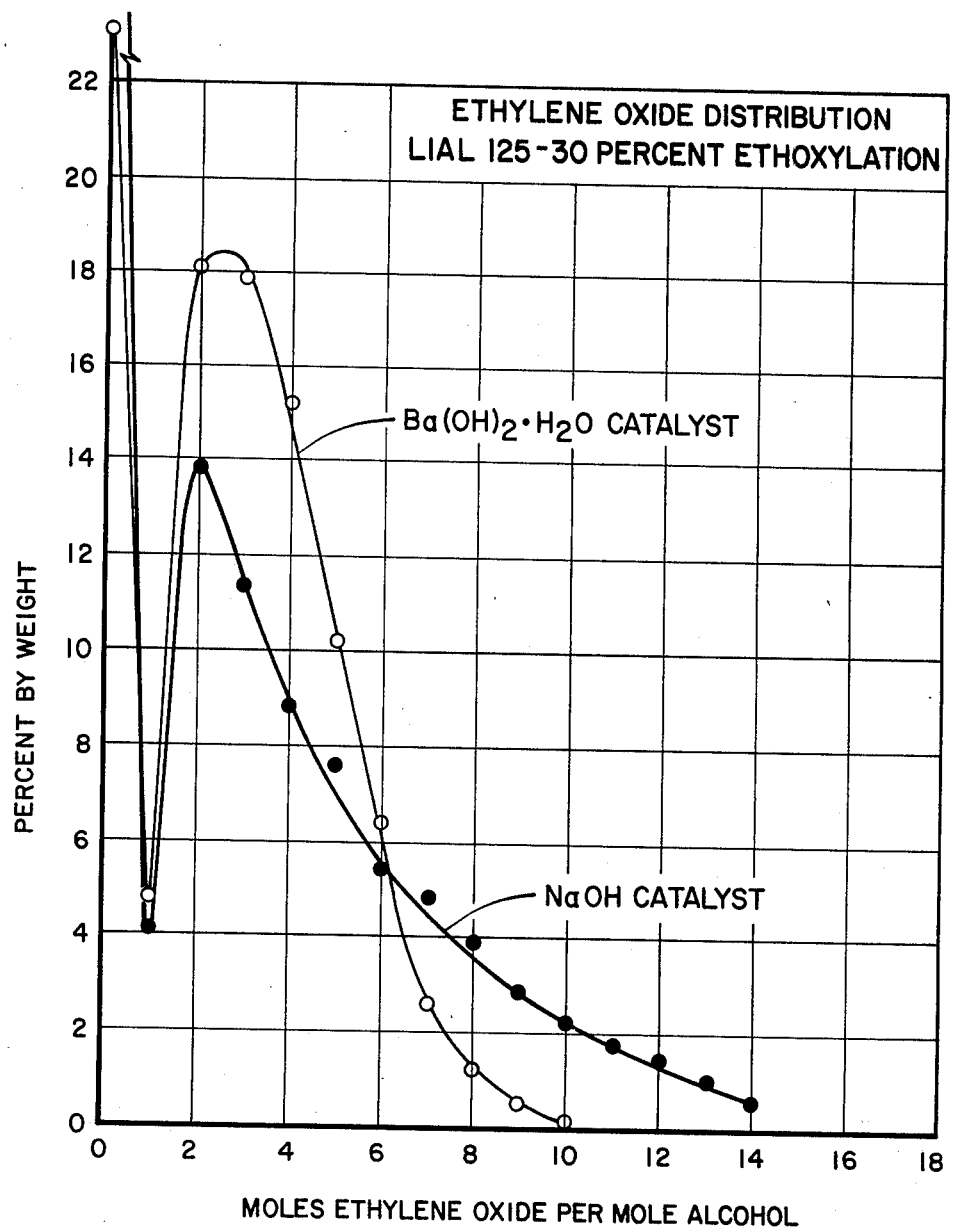
Figure 6:
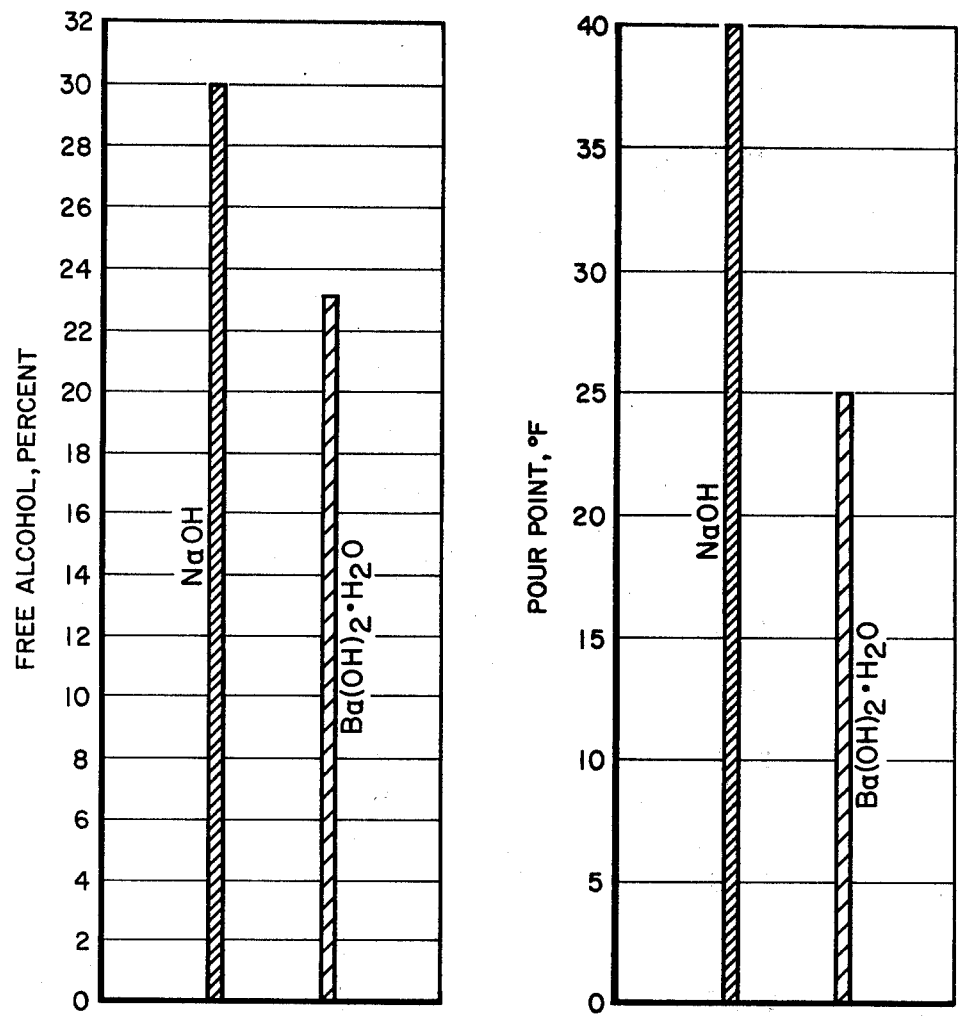

An experiment was performed as in Example 9 but with LIAL 125 alcohol (210 g) and 90 g (30% ethoxylation) of ethylene oxide. EO distribution, free alcohol and pour point data from the resulting LIAL 125-30 ethoxylate are shown in FIGS. 5 and 6.

EXAMPLE 12

An experiment was performed as in 10 except with 210 g of LIAL 125 alcohol and 90 g of ethylene oxide. EO distribution, free alcohol, and pour point data are compared with those from Example 11 in FIGS. 5 and 6.

EXAMPLE 13

Figure 7:
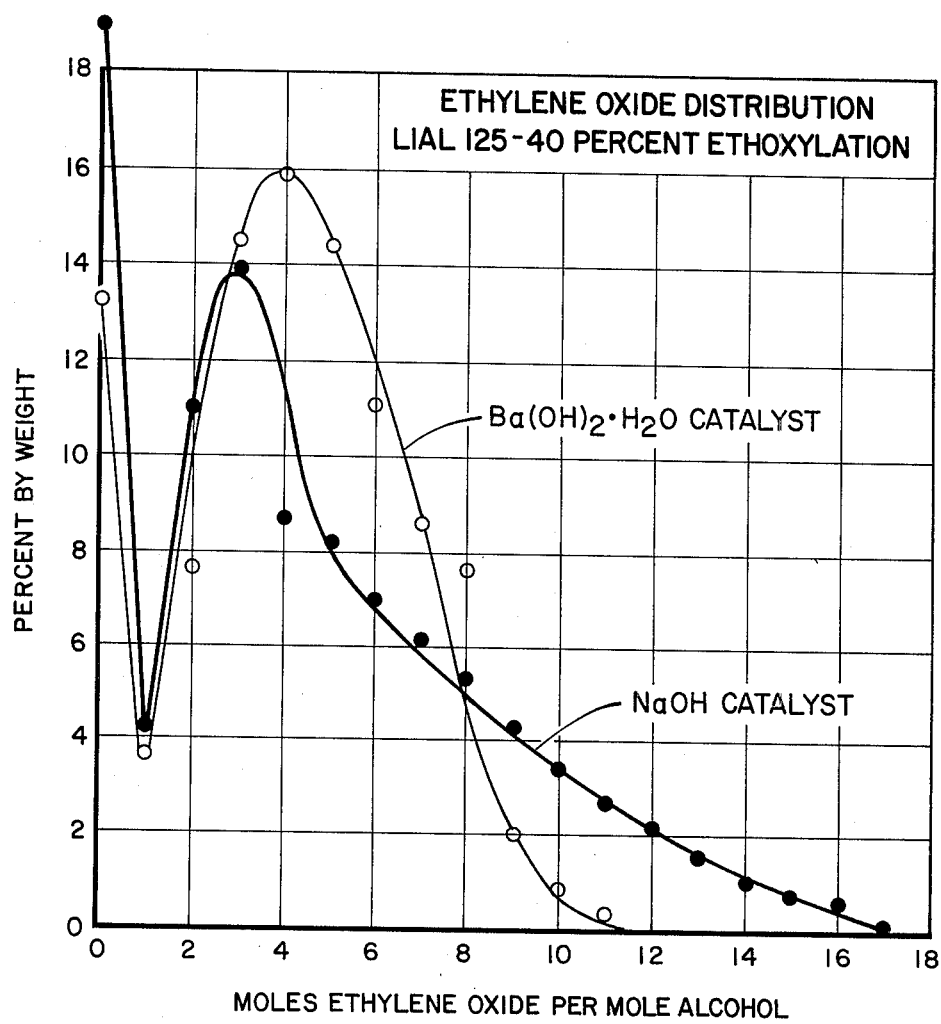
Figure 8:
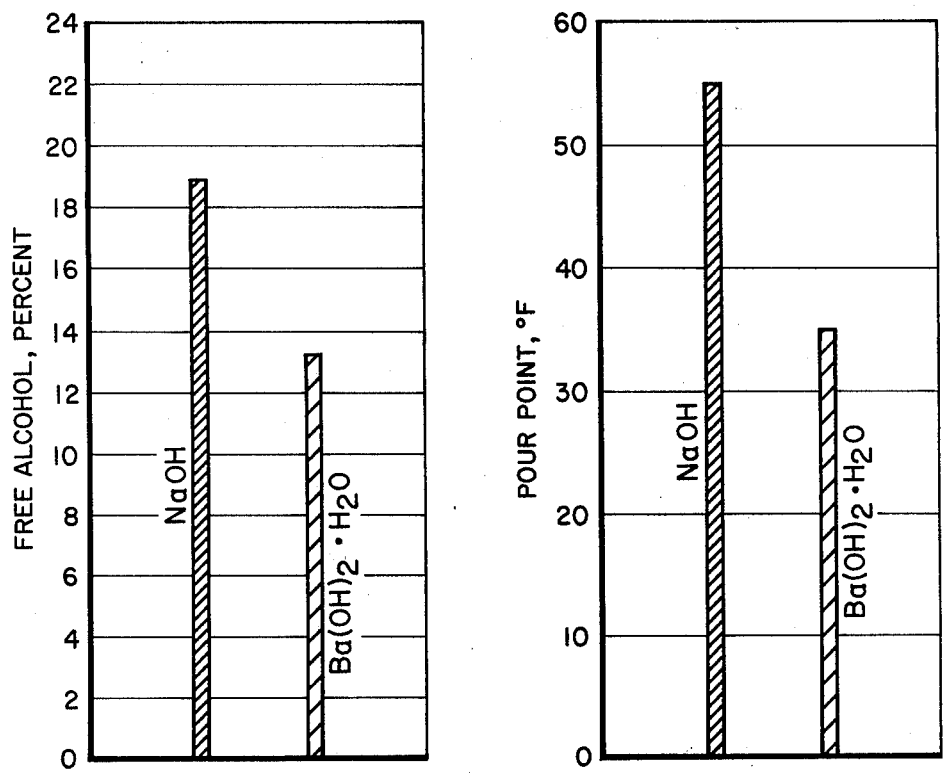

An experiment was performed as in Example 9 but with 180 g LIAL 125 alcohol and 120 g ethylene oxide (40% ethoxylation). EO distribution, free alcohol, and pour point data from the resulting LIAL 125-40 ethoxylate are shown in FIGS. 7 and 8.

EXAMPLE 14

An experiment was performed as in Example 10 except with 180 g LIAL 125 alcohol and 120 g ethylene oxide. Comparisons with data from Example 13 EO distribution, free alcohol and pour point data are made with reference to FIGS. 7 and 8.

EXAMPLE 15

Figure 9:
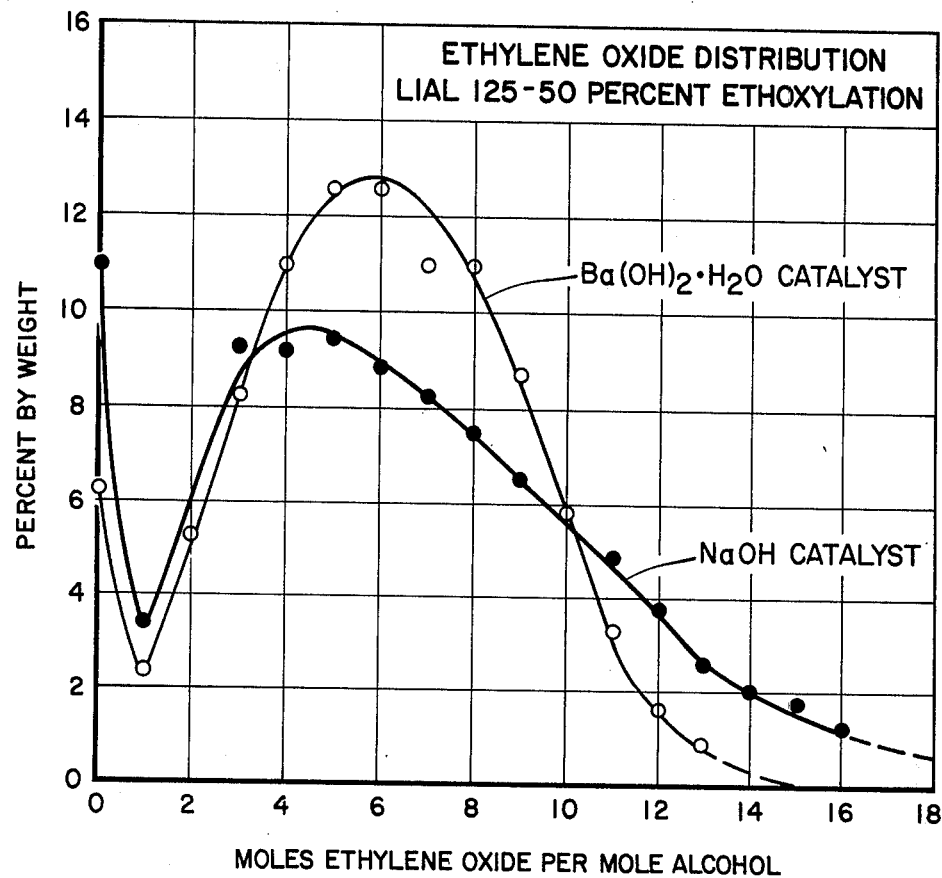
Figure 10:
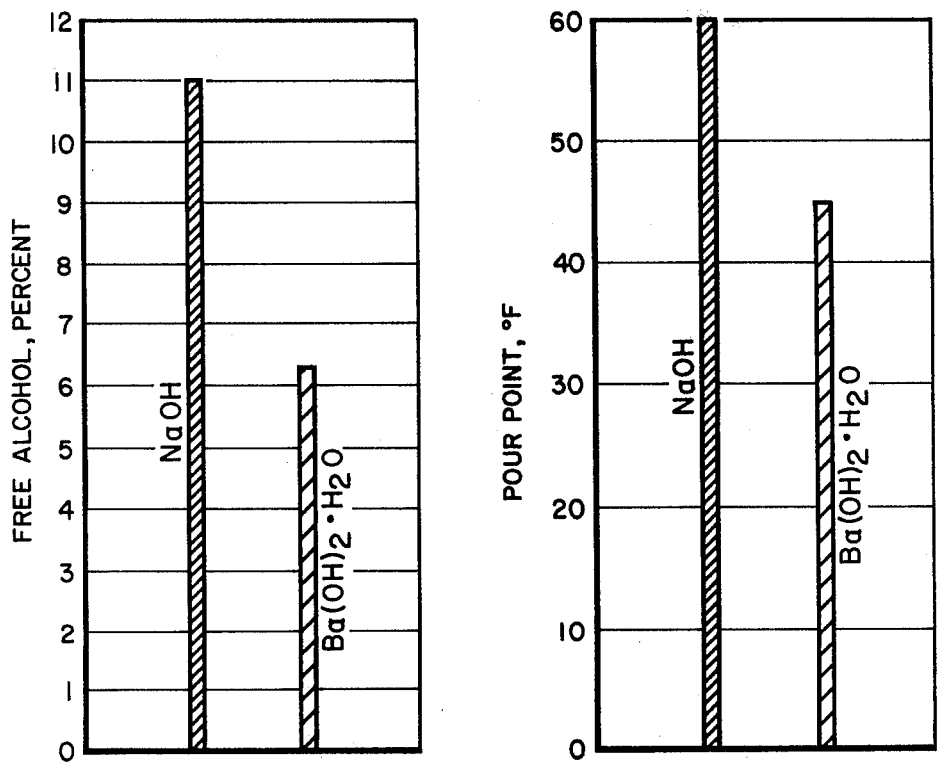

An experiment was performed as in Example 9 except with 150 g LIAL 125 alcohol and 150 g ethylene oxide (50% ethoxylation). EO distribution, free alcohol, and pour point data from the resulting LIAL 125-50 ethoxylate are shown in FIGS. 9 and 10.

EXAMPLE 16

An experiment was performed as in Example 10 except with 150 g LIAL 125 alcohol and 150 g ethylene oxide. Comparisons with data from Example 15 including EO distribution, free alcohol and pour point data are made with respect to FIGS. 9 and 10.

Thus it is apparent by practicing the instant invention high mole adduct ethoxylates of alcohols can be obtained in a very narrow, highly desirable distribution range while producing very low amounts of by-products and unreacted free alcohols.

Gas chromatographic (GLC) analysis of the experiments described above showed the basic barium-containing catalysts of the instant invention to be low in by-product and unreacted free alcohols. A comparison with NaOH showed BaO to favorably compare to the known basic catalyst. Both BaO and NaOH ethoxylation products contained less than 1 part per million (ppm) dioxane and less than 3 weight percent polyethylene glycol (based on total reaction product, and determined by solvent extraction). These basic catalysts produced reaction products far superior to those obtained in acid catalyzed ethoxylations, in which reaction product dioxane normally exceeds 1000 ppm and polyethylene glycol exceeds 3 weight percent.

The barium-containing catalysts of the instant invention excel in the low levels of unreacted free alcohols in the reaction product. This superiority is clearly demonstrated in FIGS. 1 through 12, where the relative amounts of unreacted alcohol are graphically illustrated by referring to the locations of the respective graphs as they intersect the zero/ethylene oxide number axid. The distance between the point of intersection and the ordinate of the graph (0,0 value) indicates the free alcohols present. The unreacted free alcohols present in BaO catalyzed reaction products is only about 30% of that present in NaOH catalyzed reaction product. The figures also show the improved pour points and EO distribution obtained when carrying out the instant invention.

Although exemplified as a batch reaction, the catalysts of the instant invention are also extremely well-suited to continuous reaction methods since the reaction products are of extremely desirable quality and quantity.

While certain embodiments and details have been shown for the purpose of illustrating this invention, it will be apparent to those skilled in this art that various changes and modifications may be made herein without departing from the spirit or scope of the invention.

I claim:

1. A method for the ethoxylation of alkanols comprising contacting said alkanols with ethylene oxide in the presence of a catalyst selected from the group consisting of barium oxide, barium hydroxide, hydrated barium hydroxide or barium metal at a temperature of from about 200° F. to about 500° F.

2. A method as described in claim 1 wherein the catalyst is selected from the group consisting of barium oxide or hydrated barium hydroxide.

3. A method as described in claim 2 wherein the alkanol is a product of a hydroformylation/hydrogenation reaction.

4. A method as described in claim 3 wherein the alkanol is a product of a hydroformylation/hydrogenation reaction.

5. A method as described in claim 4 wherein the reaction is carried out at a pressure up to about 100 pounds per square inch gauge (psig).

6. A method as described in claim 5 wherein the ethylene oxide mole adduct ranges from about 30 weight percent to about 80 weight percent of the ethoxylated product.

7. A method as described in claim 6 wherein the barium-containing catalyst is present in an amount from aobut 0.1 to bout 0.5% by weight based upon the alkanol to be reacted.

8. A method as described in claim 2 when carried out as a continuous reaction.

9. A method as described in claim 6 wherein the alkanol is a linear primary alcohol containing from about 8 to about 16 carbon atoms, the ethylene oxide is present in an amount of from about 40 to about 70 percent, temperature is about 350° C., the pressure is about 50 psig, and the barium-containing catalyst is present in a concentration of from about 0.1 to about 0.5% based on the weight of the alcohol to be reacted.

* * * * *